United States Patent
Bartlow et al.

(10) Patent No.: US 10,408,722 B2
(45) Date of Patent: Sep. 10, 2019

(54) PROOF TESTING BRITTLE COMPONENTS OF ELECTRONIC DEVICES

(71) Applicant: Apple Inc., Cupertino, CA (US)

(72) Inventors: Christopher C. Bartlow, Cupertino, CA (US); Dale N. Memering, Cupertino, CA (US)

(73) Assignee: APPLE INC., Cupertino, CA (US)

( * ) Notice: Subject to any disclaimer, the term of this patent is extended or adjusted under 35 U.S.C. 154(b) by 317 days.

(21) Appl. No.: 15/280,514

(22) Filed: Sep. 29, 2016

(65) Prior Publication Data
US 2017/0089818 A1    Mar. 30, 2017

Related U.S. Application Data

(60) Provisional application No. 62/234,931, filed on Sep. 30, 2015.

(51) Int. Cl.
*G01N 3/20* (2006.01)
*G01M 99/00* (2011.01)

(52) U.S. Cl.
CPC .............. *G01N 3/20* (2013.01); *G01M 99/00* (2013.01)

(58) Field of Classification Search
CPC ........................................................ G01N 3/20
USPC .......................................................... 73/849
See application file for complete search history.

(56) References Cited

U.S. PATENT DOCUMENTS

| | | | | |
|---|---|---|---|---|
| 5,500,535 A | * | 3/1996 | Jing | B82Y 35/00 250/440.11 |
| 5,583,298 A | * | 12/1996 | Walsh | B29C 70/525 73/831 |
| 5,610,846 A | * | 3/1997 | Trapet | G01B 21/045 702/41 |
| 5,892,157 A | | 4/1999 | Syre | |
| 6,424,137 B1 | | 7/2002 | Sampson | |
| 6,673,478 B2 | | 1/2004 | Kato et al. | |
| 7,554,654 B2 | | 6/2009 | Meeks et al. | |
| 7,861,573 B1 | | 1/2011 | Tenaglia | |

(Continued)

FOREIGN PATENT DOCUMENTS

| | | |
|---|---|---|
| CN | 1647228 | 7/2005 |
| CN | 203014915 | 6/2013 |

(Continued)

OTHER PUBLICATIONS

Gorla et al., "Structural, optical, and surface acoustic wave properties of epitaxial ZnO films grown on (0112) sapphire by metalorganic chemical vapor deposition," Journal of Applied Physics, vol. 85, No. 5, pp. 2594-2602, Mar. 1, 1999.

*Primary Examiner* — Daniel S Larkin
(74) *Attorney, Agent, or Firm* — Dorsey & Whitney LLP

(57) ABSTRACT

Methods and a system for proof testing brittle components of electronic devices are disclosed. The method may include positioning the brittle component relative to a probe of a testing system, contacting the probe to a surface of the brittle component at a first location, and applying a first force at the first location using the probe to create a first localized tensile band below the surface of the brittle component. The method may also include contacting the probe to the surface of the brittle component at a second location, distinct from the first location, and applying a second force at the second location using the probe to create a second localized tensile band below the surface of the brittle component.

19 Claims, 12 Drawing Sheets

(56) References Cited

U.S. PATENT DOCUMENTS

| | | | |
|---|---|---|---|
| 2006/0162456 A1* | 7/2006 | Kennedy | G01N 29/225 |
| | | | 73/620 |
| 2013/0237402 A1 | 9/2013 | Wang et al. | |
| 2014/0182392 A1* | 7/2014 | Woodhull | B24B 37/02 |
| | | | 73/851 |
| 2015/0089792 A1 | 4/2015 | Memering et al. | |
| 2015/0226723 A1 | 8/2015 | Memering et al. | |
| 2017/0059463 A1* | 3/2017 | Luzzato | G01N 3/20 |

FOREIGN PATENT DOCUMENTS

| | | |
|---|---|---|
| JP | H02118615 | 5/1990 |
| JP | H04109709 | 4/1992 |
| JP | H10326385 | 12/1998 |

* cited by examiner

PROOF TESTING BRITTLE COMPONENTS OF ELECTRONIC DEVICES

CROSS-REFERENCE TO RELATED APPLICATION

This application is a nonprovisional patent application of and claims the benefit to U.S. Provisional Patent Application No. 62/234,931, filed Sep. 30, 2015 and titled "Proof Testing Brittle Components of Electronic Devices," the disclosure of which is hereby incorporated herein by reference in its entirety.

FIELD

The disclosure relates generally to testing materials and more particularly to methods for proof testing brittle components of electronic devices and proof testing systems.

BACKGROUND

Current electronic devices continue to become more prevalent in day-to-day activities. For example, smart phones and tablet computers continue to grow in popularity and provide everyday personal and business functions to their users. These electronic devices typically include input components, such as buttons or screen displays, that may be utilized by a user to interact (e.g., input/output) with the electronic devices. These input components may be formed on and/or integral with the housing of the electronic device.

To maintain and/or to ensure functionality of the electronic device, input components and the housing of electronic devices may be formed from materials that may withstand conventional wear-and-tear on the electronic device. As an example, ceramic materials may be used to form the input components and/or the housing. Specific examples of the ceramic material include alumina ($Al_2O_3$) (e.g., corundum), sapphire and zirconia. Because of the unique and beneficial chemical or physical characteristics (e.g., hardness, strength), ceramic materials have become a viable material to be used in current electronic devices.

To ensure all ceramic materials used to form components of the electronic device meet quality control standards and/or will function substantially similarly between each individual device, the ceramic materials may undergo conventional material testing processes. Such material testing processes may include a material bending test. During the bending test, a piece of ceramic material is bent or flexed to detect material faults and/or flaws that may be formed in the material. However, because the bending test applies a global stress to the ceramic material when flexing the material, the results of the test may be less than accurate. For example, the ceramic material may prematurely break in a portion of the material that includes no faults or material flaws, but includes reduced strength because of features (e.g., apertures, recess) formed therein. Additionally, the ceramic material may not break in a portion of the material that includes detrimental material fault or flaw because of the way in which the global stress is formed on the ceramic material and/or the location of the material flaw in respect to the bend in the ceramic material. Further, the bending test applies a global stress to the entire ceramic material and does not differentiate between portions of the ceramic material that may be more or less susceptible to damage when implemented within the electronic device.

Therefore, it is desirable to have a material testing process that can selectively and accurately proof test a ceramic material.

SUMMARY

A method for proof testing brittle components for an electronic device is disclosed. The method comprises positioning a probe of a testing system relative to the brittle component, contacting the probe to a surface of the brittle component at a first location, and applying a first force at the first location using the probe to create a first localized tensile band below the surface of the brittle component. The method can also comprise contacting the probe to the surface of the brittle component at a second location, distinct from the first location, and applying a second force at the second location using the probe to create a second localized tensile band below the surface of the brittle component.

A method for proof testing brittle components for an electronic device is disclosed. The method comprises positioning the brittle component relative to a probe of a testing system, contacting the probe to a surface of the brittle component at a first location, moving the probe from the first location to a second location on the surface of the brittle component, and varying a force applied to the brittle component as the probe moves from the first location to the second location to create a localized tensile band below the surface of the brittle component.

A system for proof testing a brittle component is disclosed. The system comprises a rigid base support configured to receive the brittle component, and perimeter supports substantially surrounding the brittle component. The perimeter supports are configured to apply a clamping force on the brittle component toward the base support. The system also comprises a probe positioned above the base support. The probe is configured to contact a surface of the brittle component and apply a force to the brittle component. Additionally, the system comprises a gantry system coupled to the probe and configured to move the probe above the base support.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The following disclosure relates generally to testing materials and more particularly to methods for proof testing brittle components of electronic devices and proof testing systems.

In a particular embodiment, the testing system is configured to selectively apply forces to a brittle component utilized in an electronic device to determine if the brittle component meets desired quality and/or strength standards. The forces selectively applied to the brittle component use a testing probe that is configured to apply the forces in various locations on the brittle component at various magnitudes. The locations which receive the force include unique characteristics, such as varied strengths or support within the electronic device and/or locations more susceptible to damage over the operational life of the electronic device, and therefore require material testing to ensure the component can be utilized within the electronic device without risk of premature failure (e.g., cracking). Additionally, these unique characteristics determine the magnitude of the force applied at these locations. Selectively applying distinct forces in predetermined locations of a brittle component of an electronic device ensures that the testing process used to determine if the brittle component can be utilized in the electronic device is accurate, precise and does not just uniformly stress the brittle component which includes unique portions, as discussed herein.

These and other embodiments are discussed below with reference to FIGS. 1A-9. However, those skilled in the art will readily appreciate that the detailed description given herein with respect to these Figures is for explanatory purposes only and should not be construed as limiting.

Figure 1A:
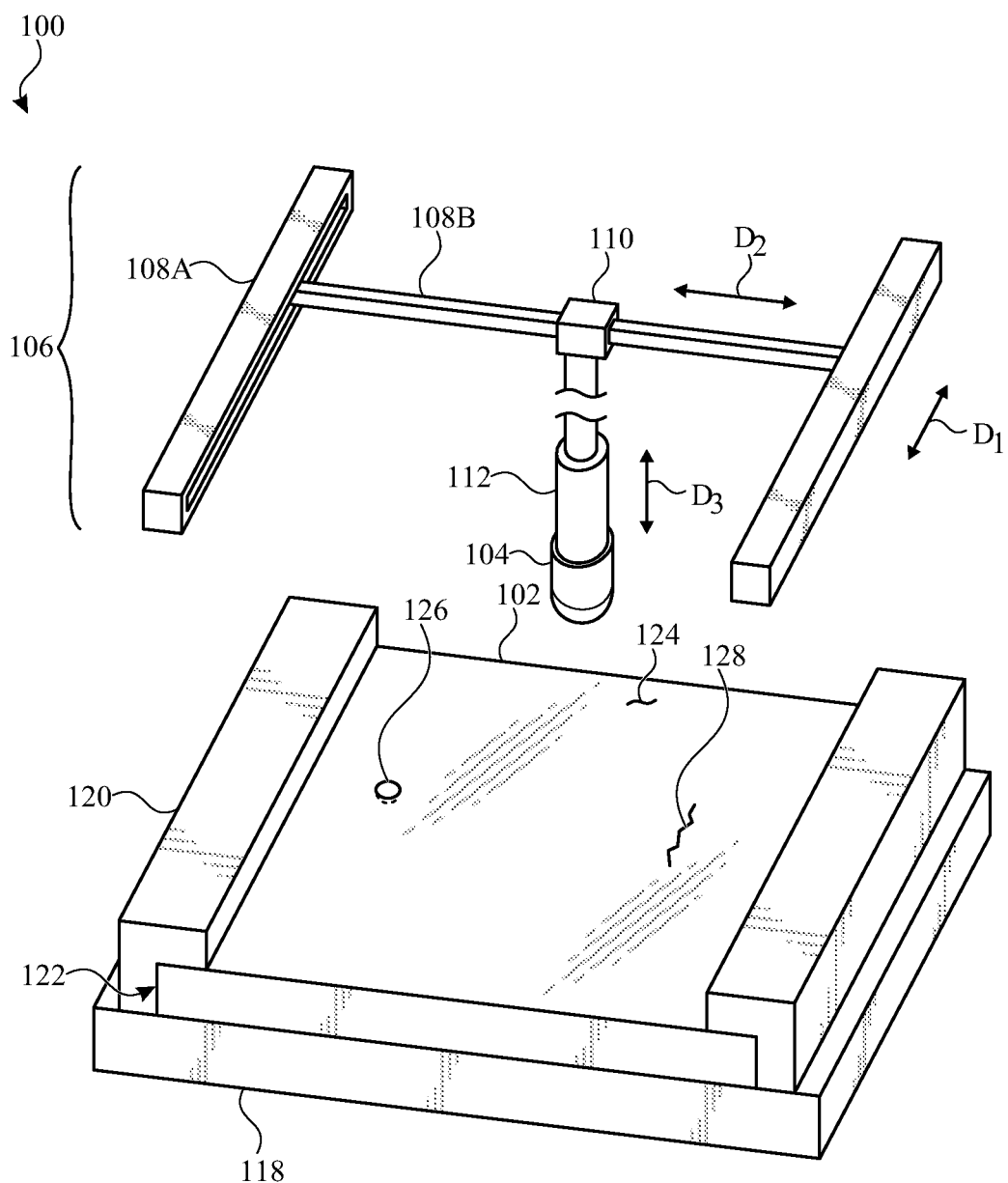
FIG. 1A shows a testing system including a probe and a brittle component for an electronic device, according to embodiments.
Figure 1B:
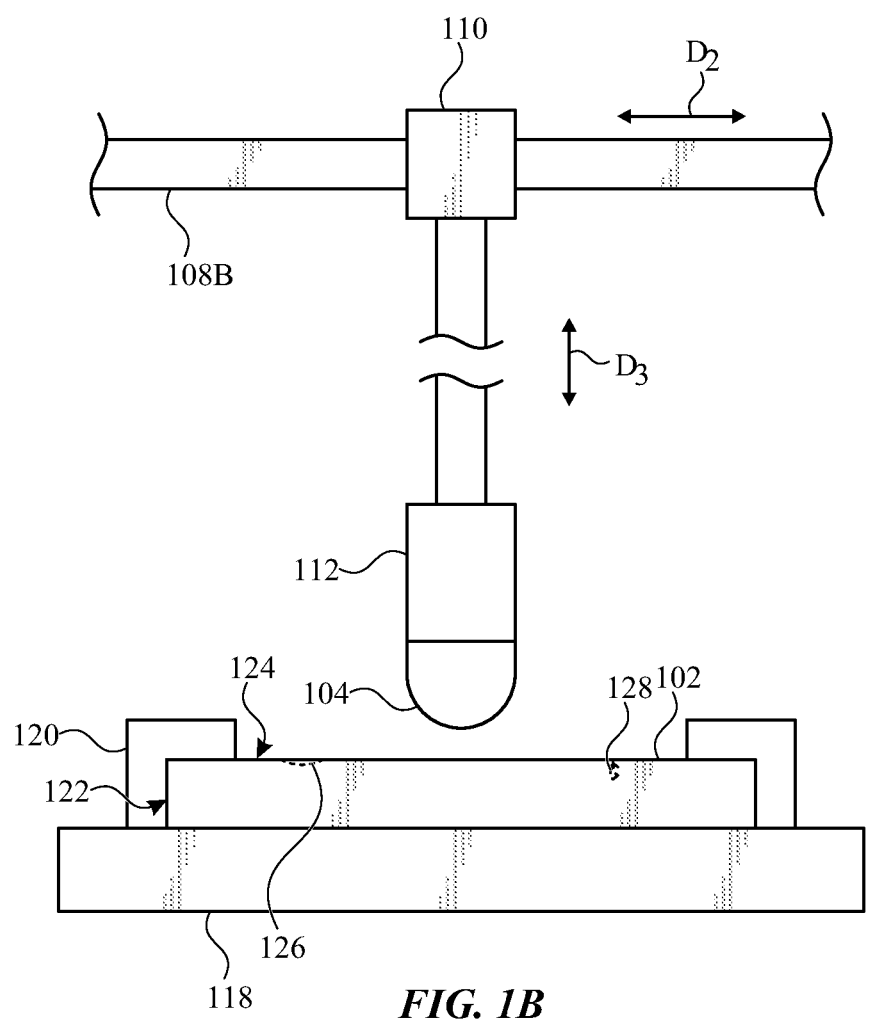
FIG. 1B shows a front view of the testing system and the brittle component of FIG. 1A, according to embodiments.

FIGS. 1A and 1B show a material testing system, according to embodiments. Testing system 100 is configured to proof test brittle materials or components 102 (hereafter, "brittle component 102") utilized by an electronic device (see, FIG. 9). Specifically, and as discussed in detail below, a test probe 104 of testing system 100 is configured to apply forces to various, distinct locations on brittle component 102 in order to determine if brittle component 102 meets desired quality and/or strength standards for implementation within an electronic device. By selectively applying distinct forces in predetermined locations of brittle component 102, testing system 100 and the testing process performed by testing system 100 can accurately and precisely determine if brittle component 102 meets quality and/or strength standards; especially in portions of brittle component 102 that include unique characteristics (e.g., portions having varied strengths, thickness or support within the electronic device, portions more susceptible to damage over the operational life of the electronic device and so on), as discussed herein.

Brittle component 102 is positioned below and/or adjacent probe 104 of testing system 100. Brittle component 102 is formed from a variety of materials that have brittle characteristics or properties. In non-limiting examples, brittle component 102 is formed from glass or ceramics, including, for example, zirconia or sapphire. Additionally, and as discussed herein, brittle component 102 can be utilized within an electronic device, and specifically, brittle component 102 can be used to form transparent covers, buttons, caps, housings or enclosures and the like for an electronic device As shown in FIGS. 1A and 1B, probe 104 of testing system 100 is positioned above brittle component 102. Probe 104 is coupled to a gantry system 106 configured to move probe 104 in various directions in order for probe to contact and/or apply a force to brittle component 102 in distinct locations when proof testing brittle component 102. As shown in FIGS. 1A and 1B, and discussed in detail with respect to FIG. 2A, probe 104 includes a substantially spherical or curved contact portion (see, FIG. 2A; 230) that is configured to contact brittle component 102 during the proof testing process discussed herein.

Probe 104 is formed from various materials. In a non-limiting example, probe 104 is formed from a substantially rigid material. In non-limiting examples, the rigid material used to form probe 104 is substantially dense, substantially tough (e.g., strength, ductility and so on), and/or substantially hard. In non-limiting examples, probe 104 is formed from plastic, glass, metal, alloys and any other suitable material. In another non-limiting example, probe 104 is formed from a substantially compliant material. In non-limiting examples, the compliant material forming probe 104 is substantially elastic, substantially dense, substantially resilient, and/or has substantial compressive strength. With comparison to the rigid material, which may require probe 104 to be substantially hard, probe 104 formed from the complaint material may be substantially elastic and/or flexible. The elasticity and/or flexibility of the compliant material allows probe 104 to deform and increase the contact area formed between probe 104 and brittle component 102 during the proof testing process. In non-limiting examples, probe 104 is formed from rubber, neoprene, silicone, polyurethane, and/or any other elastomer or substantially compliant material.

Gantry system 106 of testing system 100 includes a variety of components configured to aid in the movement of probe 104 and application of the force applied to brittle component 102 by probe 104. As shown in FIG. 1A, gantry system 106 includes tracks 108A, 108B configured to move probe 104 in a first direction ($D_1$). Specifically, side tracks 108A are positioned on opposite sides of probe 104, and a cross-track 108B is coupled to the bottom of side tracks 108A and probe 104. Cross-track 108B is configured to slide and/or move within side tracks 108A in the first direction ($D_1$). As a result, probe 104 coupled to cross-track 108B via slider 110 of gantry system 106 is also configured to move in the first direction ($D_1$) with cross-track 108B.

Slider 110 is coupled to cross-track 108B of gantry system 106, and is coupled to probe 104 via piston 112. That is, a moveable piston of gantry system 106 is coupled to both slider 110 and probe 104, such that the probe 104 is in turn coupled to slider 110 and configured to move with slider 110. As shown in FIG. 1A, slider 110 is configured to move or slide along cross-track 108B in a second direction ($D_2$), perpendicular to the first direction ($D_1$). As a result of probe 104 being coupled to slider 110 via piston 112, probe 104 is also configured to move in the second direction ($D_2$).

Piston 112 coupled to slider 110 and probe 104, respectively, includes a moveable piston or hydraulic that is configured to move probe 104 of testing system 100 in a third direction ($D_3$). As shown in FIGS. 1A and 1B, the third direction ($D_3$) is distinct from both the first direction ($D_1$) and the second direction ($D_2$). In a non-limiting example shown in FIGS. 1A and 1B, the third direction ($D_3$) is toward and/or away from brittle component 102. Additionally, because piston 112 is configured to move probe 104 in the third direction ($D_3$) toward and/or away from brittle component 102, piston 112 is also configured to move probe 104 and apply the force(s) to brittle component 102 during the proof testing process discussed herein.

As a result of gantry system 106 and its various components (e.g., tracks 108A, 108B, slider 110, piston 112), probe 104 of testing system 100 is configured to move in three directions when performing the proof testing process on brittle component 102, as discussed herein.

As shown in FIGS. 1A and 1B, testing system 100 also includes a rigid, base support 118 (hereafter, "base support 118") receiving brittle component 102. That is, brittle component 102 is positioned on base support 118 of testing system 100 and both brittle component 102 and base support 118 are positioned below probe 104 of testing system 100. Base support 118 is formed from a substantially rigid material and/or includes substantially rigid properties. As a result of the rigid material and/or rigid properties, base support 118 is not deformed and/or deflected when probe 104 applies a force to brittle component 102 during the proof testing process discussed herein. In non-limiting examples, base support 118 is formed from plastic, glass, metal, alloys and any other suitable rigid material.

Additionally, although shown herein as being coupled to probe 104, it is understood that gantry system 106 can also be coupled to base support 118 for moving brittle component 102. That is, in distinct non-limiting examples, base support 118 and probe 104, or just base support 118, can be coupled to gantry system 106 and can be configured to move brittle component 102 in various directions with respect to probe 104 to allow probe 104 to contact brittle component 102 during the testing process.

Perimeter supports 120 are coupled to base support 118 and substantially surround brittle component 102. As shown in FIGS. 1A and 1B, two perimeter supports 120 are positioned on opposite sides of brittle component 102 and substantially cover ends or edges 122 of brittle component 102. Perimeter supports 120 are configured to apply a clamping force on brittle component 102 toward base support 118. The clamping force applied by perimeter supports 120 to brittle component 102, and specifically edges 122 of brittle component 102, prevents brittle component 102 from bending or deforming when a force is applied to brittle component 102 during the testing process discussed herein. Additionally, perimeter supports 120 prevent edges 122 of brittle component 102 from lifting off of base support 118 when a force is applied to brittle component 102 by probe 104 of testing system 100. Although only two are shown, it is understood that testing system 100 can include more than two perimeter supports 120.

As a result of the various processes performed on the ceramic material to form brittle component 102 and/or because of the physical characteristics (e.g., brittleness) of brittle component 102, brittle component 102 can include surface defects on contact surface 124. The surface defects formed in or on contact surface 124 of brittle component 102 may substantially and/or negatively impact (e.g., weaken) the physical and material characteristics of brittle component 102. The surface defects formed in or on contact surface 124 are substantially small, and may not be visible or detected during a visual (e.g., naked-eye) inspection of brittle component 102. As such, the defects can be considered micro-defects. Although undetectable, these surface defects over the operational life of the electronic device utilizing brittle component 102 can grow or propagate through brittle component 102, and negatively impact the operation of brittle component 102 and/or an electronic device.

In non-limiting examples shown in FIGS. 1A and 1B, surface defects may include one or more chips 126 or cracks 128 formed on or in contact surface 124 of brittle component 102. Chip 126 and crack 128, shown in phantom in FIG. 1B, extend at least partially through brittle component 102. Chip 126 and crack 128 may be formed due to normal wear and tear and handling of brittle component 102 prior to proof testing and can be implemented within an electronic device, as discussed herein.

Figure 2A:
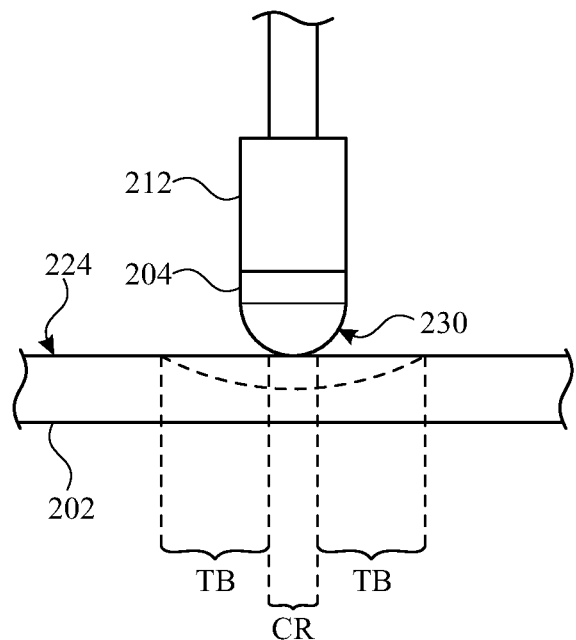
FIG. 2A shows a front view of a test probe of a testing system and a portion of a brittle component for an electronic device, according to embodiments.
Figure 2B:
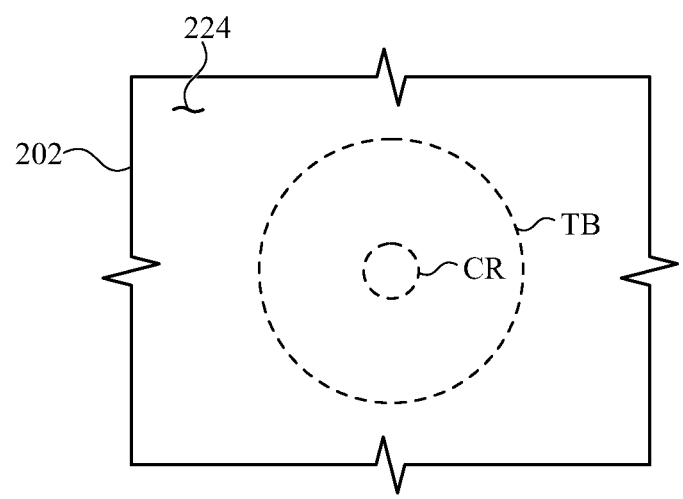
FIG. 2B shows a top view of a contact area formed on the brittle component by the test probe of FIG. 2A, according to embodiments.

FIGS. 2A and 2B show a force being applied to brittle component 202 by probe 204 when proof testing brittle component 202, as discussed herein. Specifically, FIG. 2A shows a front view of probe 204 applying a force to brittle component 202 and the various compressed and stressed regions formed therein as a result. FIG. 2B shows a top view of the compressed and stressed regions formed in the brittle component 202 when probe 204 applies a force to brittle component 202. Probe 204 is omitted from FIG. 2B for clarity.

As shown in FIG. 2A, substantially spherical or circular contact portion 230 of probe 204 contacts and/or applies a force to contact surface 224 of brittle component 202. Spherical contact portion 230 of probe 204 is configured to form a substantially circular contact area on contact surface 224 of brittle component 202 when performing the proof testing process discussed herein.

As shown in FIGS. 2A and 2B, when piston 212 of a gantry system (see, e.g., gantry system 106 of FIG. 1A) moves probe 204 in a third direction ($D_3$) (see, FIG. 1A) toward contact surface 224 and applies a force to brittle component 202, portions of brittle component 202 formed below contact surface 224 and/or probe 204 are affected. In a non-limiting example, a compressed region (CR) is formed in a portion of brittle component 202 when probe 204 applies a force to brittle component 202. As shown in FIG. 2A, the compressed region (CR) is formed below contact surface 224, and is substantially aligned with probe 204 contacting brittle component 202. Additionally, in the non-limiting example, the compressed region (CR) is substantially aligned with the portion of substantially spherical or circular contact portion 230 of probe 204 contacting brittle component 202. The compressed region (CR) is formed in brittle component 202 as a result of the force applied by probe 204 compressing the contacted portion of brittle component 202.

In the non-limiting example shown in FIGS. 2A and 2B, localized tensile band (TB) is also formed within a portion of brittle component 202 when probe 204 applies a force to brittle component 202. Tensile band (TB) is formed below contact surface 224, and is formed substantially adjacent probe 204 contacting brittle component 202. As shown in FIGS. 2A and 2B, tensile band (TB) is also positioned adjacent to and/or substantially surrounds compressed region (CR) formed in brittle component 202. Tensile band (TB) is formed in brittle component 202 as a result of forming compressed region (CR) in brittle component 202 when the force is applied by probe 204.

As shown in FIGS. 2A and 2B, the tensile band (TB) formed in brittle component 202 is substantially larger in width than the compressed region (CR). Additionally, as shown in FIG. 2A, the depth or magnitude of the tensile band (TB) decreases as the distance from the compressed region (CR) increases. Specifically, at the transition line between the compressed region (CR) and the tensile band (TB), the depth or magnitude of each of the compressed region (CR) and tensile band (TB) is substantially equal. However, as the distance within the tensile band (TB) increases from the compressed region (CR), the depth or magnitude of the tensile band decreases. The size, width, depth and/or magnitude of the compressed region (CR) and tensile band (TB) formed in brittle component 202 when probe 204 applies a force is dependent on, at least in part, the size of probe 204 and/or contact portion 230, the shape of contact portion 230 of probe 204, the material composition of brittle component 202, the magnitude of the force applied by probe 204 and so on.

Figure 3:
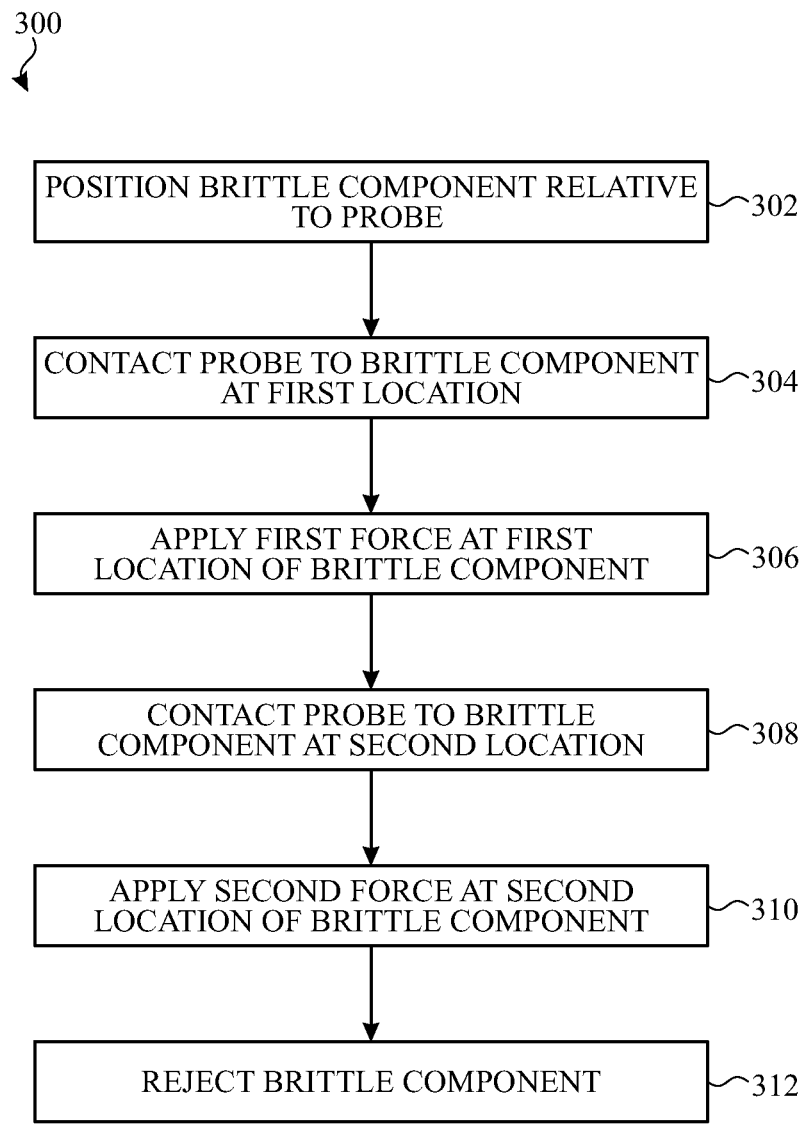
FIG. 3 shows a flow chart of an example process for proof testing brittle components for an electronic device, according to embodiments.

FIG. 3 depicts an example process for proof testing a component. Specifically, FIG. 3 is a flowchart depicting one example process 300 for proof testing a brittle component for an electronic device. In some cases, the brittle component is formed from a ceramic material, as discussed herein respect to FIGS. 1A and 1B and can be utilized within an electronic device discussed below with respect to FIG. 9.

In process 302, a brittle component is positioned relative to a probe of a testing system. The brittle component can take the form of a component utilized by an electronic device and can be formed from a brittle, ceramic material including, but not limited to, alumina, sapphire or zirconia. The brittle component can include surface defects (e.g., chips, cracks) formed on a surface and/or partially through the brittle component. These surface defects are typically small enough (e.g., micro-cracks) to go undetected when visually inspecting the brittle component.

Positioning the brittle component relative to the probe can also include securing the brittle component to a rigid base support. The rigid base support prevents the brittle component from deflecting or bending when the probe applies a force to the brittle component (e.g., process 306, process 310), as discussed herein. Additionally, positioning the brittle component relative to the probe also includes preventing or restraining edges of the brittle component from bending when a force is applied to the brittle component by the probe. The edges can be restrained by perimeter supports surrounding the brittle component and coupled to the edges of the brittle component. The perimeter supports prevent or restrain the edges of the brittle component by providing a clamping force on the brittle component toward the rigid base support.

In process 304, the probe of the testing system contacts the brittle component at a first location. Specifically, the probe is moved to contact a surface of the brittle component at a first location of the brittle component. The probe is moved to contact the brittle component at the first location by a gantry system. The first location of the brittle component which the probe contacts can be a random location on the brittle component or can be a predetermined location. Where the first location is predetermined, the first location can include a feature (e.g., aperture) formed in the brittle component, and/or can include a portion of the brittle component that is supported by internal components or portions of the electronic device. Additionally, the first location can also include a surface defect formed in the brittle component.

In process 306, a first force is applied to the brittle component at the first location. The first force is applied to the brittle component using the probe of the testing system. Applying the first force at the first location of the brittle component can create a compressed region and a localized tensile band in the brittle component. The compressed region is formed in the brittle component below and/or aligned with the probe contacting the surface of the brittle component. The tensile band is created below the surface of and/or partially within the brittle component. The tensile band is also positioned adjacent and/or substantially surrounds the compressed region created in the brittle component.

Applying the first force in process 306 also includes applying the first force for a predetermined time to (potentially) propagate, grow and/or spread a surface defect formed in the brittle component. Specifically, the first force is applied to the first location of the brittle component for a predetermined time, such that if a surface defect exists in a portion of the brittle component that includes the compressed region and/or the tensile band, the surface defect would propagate through at least a portion of the brittle component. As a result of propagating the surface defect through at least a portion of the brittle component, the surface defect can now be seen in the brittle component. That is, the previously undetected (e.g., not visible) surface defect formed in the brittle component becomes visible subsequent to applying the first force for the predetermined time and propagating the surface defect through at least a portion of the brittle component. The predetermined time for applying the first force to the brittle component is dependent on, at least in part, operational characteristics of the testing system (e.g., size of test probe, size of contact area between the test probe and the brittle component, the magnitude of the force applied to the brittle component and so on) and/or material characteristics of the brittle component (e.g., material composition, features formed adjacent the first location, material thickness and so on).

In process 308, the probe of the testing system contacts the brittle component at a second location, distinct from the first location in process 304. Specifically, the probe is moved to contact the surface of the brittle component at a second location of the brittle component that is distinct from the first location. Similar to process 304, the second location of the brittle component which the probe contacts can be a random location on the brittle component or can be a predetermined location. Where the second location is predetermined, the second location can include a feature (e.g., aperture) formed in the brittle component, and/or can include a portion of the brittle component that is supported by internal components or portions of the electronic device. Additionally, the second location can also include a surface defect formed in the brittle component.

Although not shown in FIG. 3, intermediate steps or processes can take place between applying the first force to the brittle component at the first location and contacting the brittle component at the second location. That is, the process can include moving the probe from the first location on the surface of the brittle component to the second location. As discussed herein, the probe is moved using the gantry system. The moving of the probe from the first location to the second location can include lifting the probe from the first location after applying the first force for the predetermined time, and moving the probe to above the second location without contacting the brittle component. Once positioned above the second location, the probe can contact the brittle component at the second location.

In an additional non-limiting example, while moving the probe from the first location to the second location, constant contact between the surface of the brittle component and the probe can be maintained. The contact can be maintained by implementing a roller feature, such as a ball bearing, on the contact portion of the probe, or simple moving or sliding the substantially spherical contact portion of the probe along the surface of the brittle component. As discussed herein in detail, maintaining constant contact between the brittle component and the probe while moving the probe from the first location to the second location can also allow the probe to apply a force, constant or variable, to the portions of the brittle component positioned between the first location and the second location. This can allow improved material testing and testing a larger area of the brittle component to determine if the brittle component is capable of being used within an electronic device, as discussed herein.

In process 310, a second force is applied to the brittle component at the second location. The second force can be similar or different in magnitude than the first force applied to the brittle component at the first location in process 306. The second force is applied to the brittle component using the probe of the testing system. Similar to the first force, applying the second force at the second location of the brittle material can create a compressed region and a localized tensile band in the brittle component. The compressed region is formed in the brittle component below and/or aligned with the probe contacting the surface of the brittle component. The tensile band is created below the surface of and/or partially within the brittle component. The tensile band is also positioned adjacent and/or substantially surrounds the compressed region created in the brittle component.

Applying the second force in process 310, like applying the first force in process 306, also includes applying the second force for a predetermined time to (potentially) propagate, grow and/or spread a surface defect formed in the brittle component. Specifically, the second force is applied to the second location of the brittle component for a predetermined time, such that if a surface defect exists in a portion of the brittle component that includes the compressed region and/or the tensile band, the surface defect would propagate through at least a portion of the brittle component. As a result of propagating the surface defect through at least a portion of the brittle component, the surface defect can now be seen in the brittle component.

In process 312, the brittle component is rejected from use within an electronic device in response to a surface defect being propagated through at least a portion of the brittle component. Specifically, when the previously invisible or undetectable surface defect formed in the brittle component is propagated and/or becomes visible in response to applying the first force in process 306 and/or the second force in process 310, the brittle component has failed the testing process. As such, the brittle component is discarded and/or not used within an electronic device because it does not meet the quality and/or strength standards for the electronic device, as discussed herein.

Figure 4A:
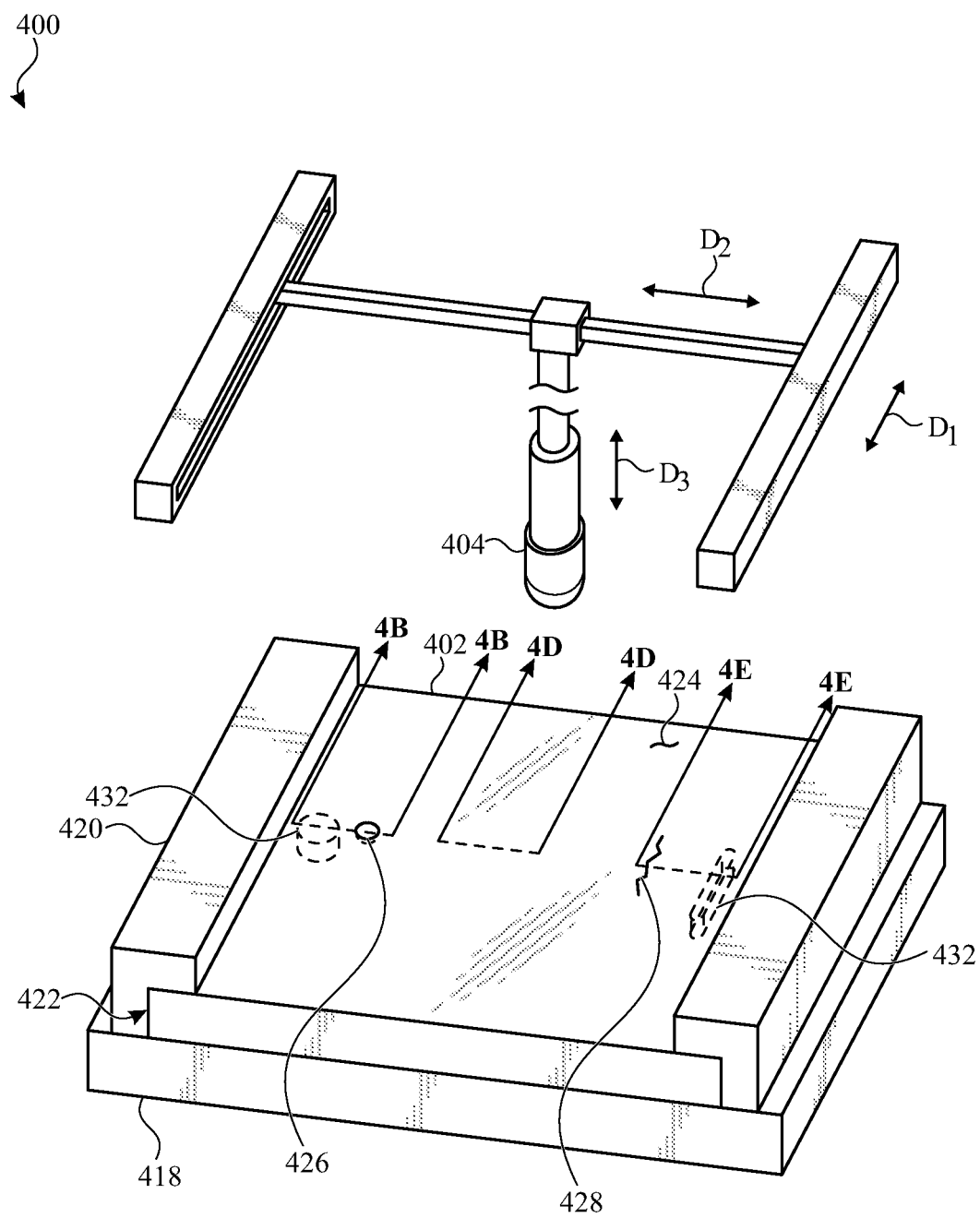
FIG. 4A shows a testing system including a probe and a brittle component for an electronic device prior to the probe contacting the brittle component at a first location, according to embodiments.

FIGS. 4A-4F show brittle component 402 undergoing the process 300 for proof testing a brittle component as shown and discussed herein with respect to FIG. 3. Testing system 400 shown in FIG. 4A is substantially similar to testing system 100 shown and discussed herein with respect to FIGS. 1A and 1B. Specifically, testing system 400 includes probe 404 positioned above brittle component 402 and configured to apply a force to contact surface 424 of brittle component 402 in various locations when performing the proof testing process. It is understood that similarly numbered and/or named components may function in a substantially similar fashion. Redundant explanation of these components has been omitted for clarity.

Additionally as shown in FIGS. 4A-4F, brittle component 402 is substantially similar to brittle component 102, 202 shown and discussed herein with respect to FIGS. 1A-2B. Specifically in FIG. 1A, brittle component 402 is positioned relative to probe 404, and secured to rigid base support 418 using perimeter supports 420 clamping edges 422. Distinct from brittle components previously discussed, brittle component 402 includes features 432, shown in phantom, formed in brittle component 402. As shown in FIG. 4A, features 432 can be formed and/or exposed on contact surface 424 of brittle component 402, and can be formed at least partially through brittle component 402. In a non-limiting example shown in FIG. 4A, features can be formed completely through brittle component 402. Features 432 are specific to the electronic device that utilizes brittle component 402. In the non-limiting example of FIG. 4A, feature 432 formed adjacent chip 426 of brittle component 402 is configured as a button aperture which can receive, housing and/or expose a button of the electronic device utilizing brittle component 402.

As discussed in detail below, the proof testing process 300 performed on brittle component 402 can include applying multiple forces to distinct locations on brittle component 402 to ensure brittle component 402 does not include surface defects (e.g., chip 426, crack 428) that will reduce the operational life of brittle component 402 and/or the electronic device. The distinct locations of brittle component 402 which receive the force applied by probe 404 include unique or distinct properties or characteristics when compared to other portions of brittle component 402. In non-limiting examples, the various locations receiving the force applied by probe 404 during the proof testing process can include, but are not limited to, distinct material strength, distinct amounts of support provided to that portion of brittle component 402 by other internal components of the electronic device and/or predetermined locations of brittle component 402 that are more susceptible to damage over the operational life of the electronic device. In a non-limiting example, and as discussed herein in detail, a first location of brittle component 402 that may receive a first force applied by probe 404 includes a portion of brittle component adjacent chip 426 and feature 432. In other non-limiting examples discussed below, a second location of brittle component 402 that receives the force applied by probe 404 can include a centralized portion of brittle component 402 formed between the features 432 and/or a portion of brittle component 402 positioned adjacent crack 428 and feature 432. As discussed herein with respect to FIG. 1A, surface defects (e.g., chip 426, crack 428) are not visible or detectable when performing a visual inspection of brittle component 402.

Additionally, and as discussed herein, the force applied to each location by probe 404 can be distinct. That is, a force applied to brittle component 402 at a first location can be distinct from the force applied to a distinct location on brittle component 402. The magnitude of the force applied to each location by probe 404 is dependent on, at least in part, the unique or distinct properties or characteristics of each location of brittle component 402. Continuing the non-limiting examples above, the first location for receiving a force applied by probe 404 positioned adjacent chip 426 and feature 432 can include a greater amount of support from additional components of the electronic device than the second location of brittle component 402 positioned adjacent crack 428 and feature 432. Additionally in the non-limiting example, first location on the brittle component 402 can include a stronger portion of brittle component 402 than the second location of the brittle component 402. The first location receiving the force from probe 404 is stronger because feature 432 is substantially circular and formed through only a small portion of brittle component 402 in the first location, and the feature 432 included in the second location is substantially elongated and formed through a larger portion of brittle component 402. As a result, the first force applied to the first location on brittle component 402 can be greater than the second force applied at the second location to ensure each location is accurately stressed and meets the quality and strength standard for implementation within the electronic device. Alternatively, the first force can be smaller than the second force to ensure the second force can withstand greater stress and/or strain without becoming damaged.

The process performed on brittle component 402 as shown and discussed herein with respect to FIG. 4A, correspond to operation 302 of the process 300 shown in FIG. 3.

Figure 4B:
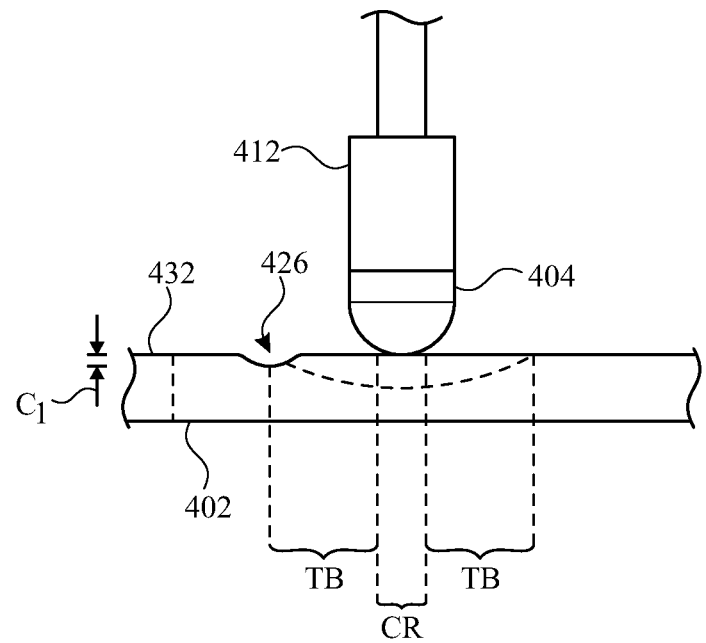
FIG. 4B shows a front view of the test probe contacting the brittle component of FIG. 4A at the first location, according to embodiments.
Figure 4C:
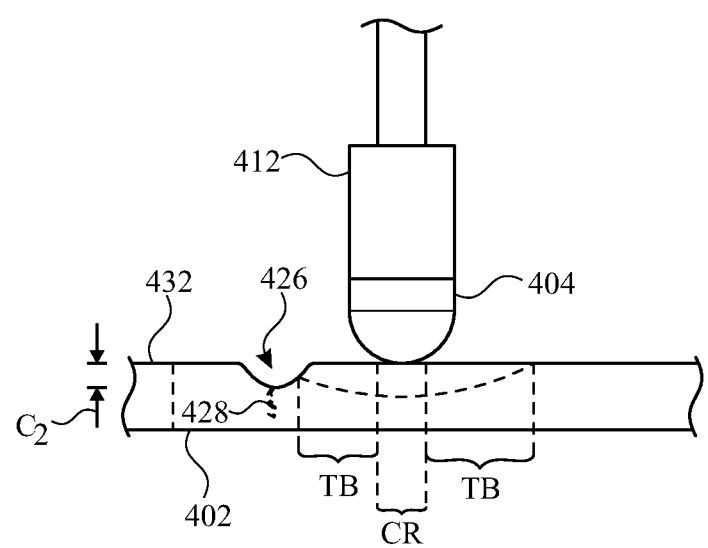
FIG. 4C shows a front view of the test probe applying a first force to the brittle component of FIG. 4A at the first location, according to embodiments.

FIGS. 4B and 4C show cross-sectional views of brittle component 402 taken along line 4B-4B of FIG. 4A. Specifically, FIG. 4B shows a cross-sectional view of a first location of brittle component 402 after probe 404 contacts brittle component 402 and probe 404 and/or piston 412 initially apply a first force to brittle component 402. Additionally, FIG. 4C shows a cross-sectional view of a first location of brittle component 402 after probe 404 and/or piston 412 apply a first force to brittle component 402 for a predetermined time. The predetermined time, as discussed above, is an amount of time that would result in the (potentially) propagation, growth and/or spreading of a surface defect (e.g., chip 426) formed in brittle component 402.

As shown in FIGS. 4B and 4C, the first location of brittle component 402 that a first force is applied includes chip 426 and feature 432, shown in phantom. Chip 426 formed partially through brittle component 402 is at least partially positioned within the tensile band (TB) formed in brittle component 402 when probe 404 applies a force to brittle component 402. That is, and as shown in FIGS. 4B and 4C, the tensile band (TB) formed or created in brittle component 402 subsequent to applying the first force to brittle component 402 using probe 404 overlaps and/or extends into chip 426 formed in brittle component 402 prior to performing the proof testing process. As a result of applying the first force in the first location for the predetermined time, as shown in FIGS. 4B and 4C, chip 426 can propagate and/or grow within brittle component 402. Comparing FIGS. 4B and 4C, the initial thickness (C0 of chip 426 formed in brittle component 402 (FIG. 4B) grows and/or propagates through brittle component 402 after the force is applied for the predetermined time, such that the final thickness ($C_2$) (FIG. 4C) of chip 426 is greater than the initial thickness (C0 of chip 426. Propagation of chip 426 can also result in a crack 428, shown in phantom, being formed in brittle component 402. The propagation of chip 426 results in chip 426 becoming visible upon inspection after performing the proof testing process, and ultimately can lead to the discarding of brittle component 402 prior to being utilized within an electronic device, as discussed herein.

The processes performed on brittle component 402 as shown and discussed herein with respect to FIGS. 4B and 4C, correspond to operations 304 and 306 of the process 300 shown in FIG. 3.

Figure 4D:
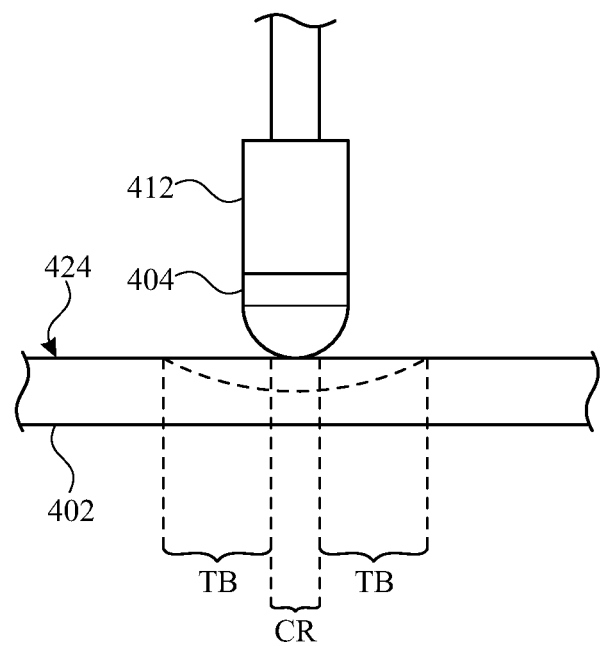
FIG. 4D shows a front view of the test probe contacting the brittle component at a second location and applying a second force to the brittle component of FIG. 4A, according to embodiments.

FIG. 4D shows a cross-sectional view of brittle component 402 taken along line 4D-4D in FIG. 4A. FIG. 4D shows a distinct, second location of brittle component 402 after probe 404 contacts brittle component 402 and probe 404 and/or piston 412 apply a second force to contact surface 424 of brittle component 402 for a predetermined time. In a non-limiting example, after probe 404 contacts and applies the first force to brittle component 402 at the first location, probe 404 is lifted from brittle component 402 and/or no longer contacts brittle component 402. Probe 404 is then moved to and positioned above the second location of brittle component 402 and subsequently moved toward brittle component 402 by piston 412 to apply the second force in the second location of brittle component 402. As shown in FIG. 4D, brittle component 402 does not include preexisting surface defects formed in the second location of brittle component 402. As a result, the second portion of brittle component 402 shown in FIG. 4D is unaffected by the second force applied by probe 404, and as discussed herein, meets quality and/or strength standards for implementation within an electronic device.

Figure 4E:
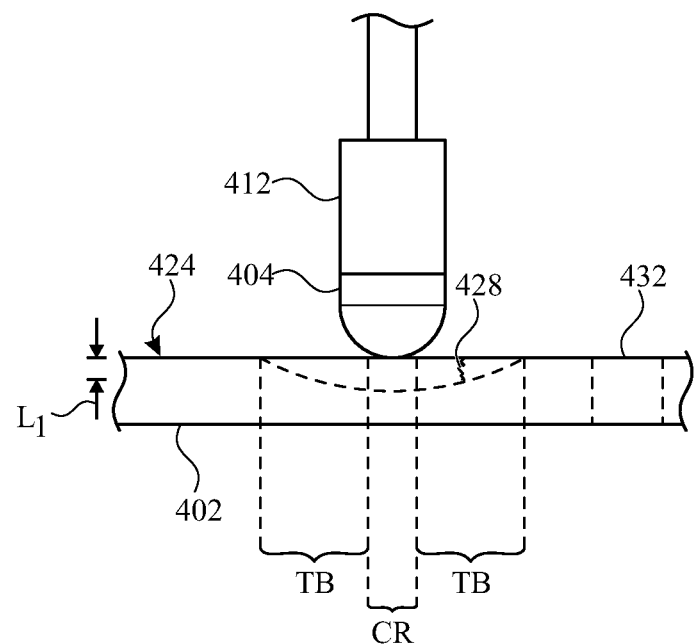
FIG. 4E shows a front view of the test probe contacting the brittle component of FIG. 4A at a second location, according to additional embodiments.
Figure 4F:
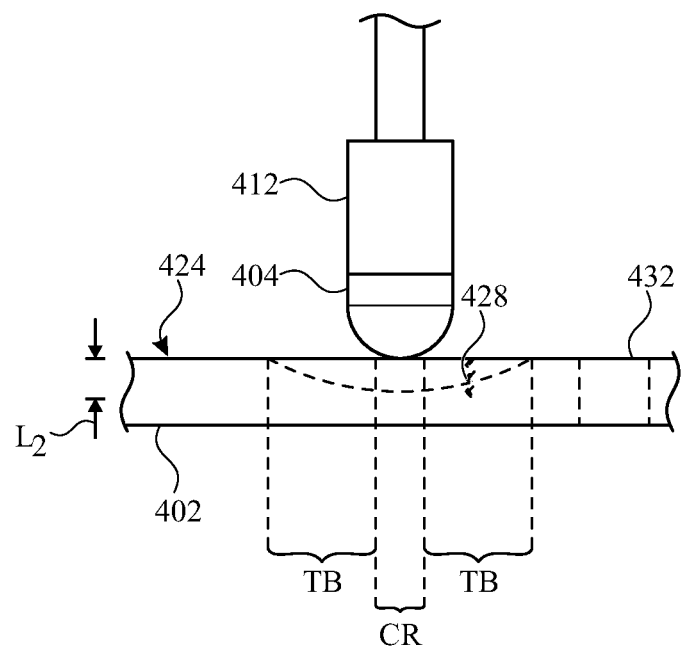
FIG. 4F shows a front view of the test probe applying a second force to the brittle component of FIG. 4A at the second location, according to additional embodiments.

Alternatively, FIGS. 4E and 4F show cross-sectional views of brittle component 402 taken along line 4E-4E of FIG. 4A. Specifically, FIG. 4E shows a cross-sectional view of another distinct (e.g., second) location of brittle component 402 after probe 404 contacts brittle component 402 and probe 404 and/or piston 412 initially apply a distinct or second force to brittle component 402. Additionally, FIG. 4F shows a cross-sectional view of the distinct location of brittle component 402 after probe 404 and/or piston 412 apply the second force to brittle component 402 for a predetermined time.

Similar to FIGS. 4B and 4C, the second location of brittle component 402 that a second force is applied includes crack 428 and feature 432, shown in phantom. As shown in FIGS. 4E and 4F, crack 428 formed partially through brittle component 402 is at least partially positioned within the tensile band (TB) formed in brittle component 402 when probe 404 applies the second force to brittle component 402. As a result of applying the second force in the second location for the predetermined time, as shown in FIGS. 4E and 4F, crack 428 propagates and/or grows within brittle component 402. Comparing FIGS. 4E and 4F, the initial length ($L_1$) of crack 428 formed in brittle component 402 (FIG. 4E) grows and/or propagates through brittle component 402 after the second force is applied for the predetermined time, such that the final length ($L_2$) (FIG. 4C) of crack 428 is greater than the initial length ($L_1$) for crack 428.

The propagation of chip 426 and/or crack 428 results in chip 426 and/or crack 428 becoming visible upon inspection after performing the proof testing process. Once chip 426 and/or crack 428 of brittle component 402 become visible, brittle component 402 may not meet a quality (e.g., aesthetic) standard by containing visible surface defects, and therefore is discarded and/or not implemented within an electronic device. Additionally and/or in conjunction within the surface defects becoming visible, the propagation of chip 426 and/or crack 428 within brittle component 402 substantially alters the physical and/or material characteristics (e.g., strength) of brittle component 402. Where the propagation of chip 426 and/or crack 428 within brittle component 402 negatively impacts (e.g., weakens) the physical and/or material characteristics of brittle component 402, the brittle component 402 may not meet material standards (e.g., strength) for implementation with the electronic device. As a result, brittle component 402 is discarded.

The processes performed on brittle component 402 as shown and discussed herein with respect to FIGS. 4D-4F, correspond to operations 308, 310 and 312 of the process 300 shown in FIG. 3.

Figure 5:
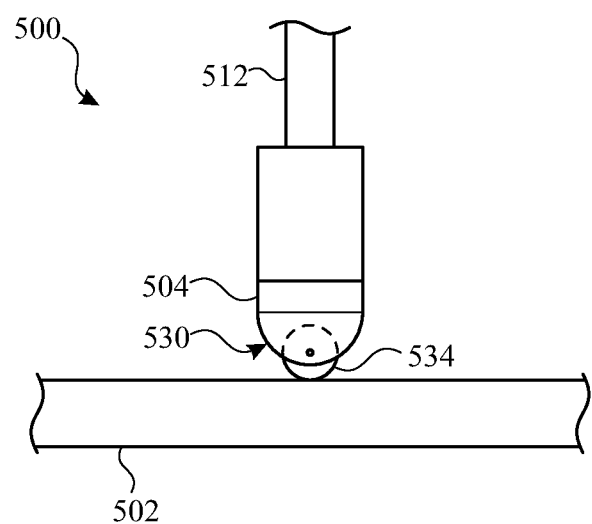
FIG. 5 shows a front view of a test probe of a testing system and a portion of a brittle component for an electronic device, according to further embodiments.

Turning to FIG. 5, probe 504 for testing system 500 is shown in another non-limiting example. Probe 504 is coupled to piston 512 and includes substantially circular and/or spherical contact portion 530 configured to form a substantially circular contact area on brittle component 502, as similarly discussed herein with respect to FIG. 2A. However, distinct from FIG. 2A, probe 504 includes additional components in a distinct configuration. Specifically as shown in FIG. 5, probe 504 includes a ball bearing 534 positioned within and/or partially exposed from probe 504. Ball bearing 534 positioned within a probe 504 includes a portion that is exposed from probe 504, and is configured to contact brittle component 502 when performing a proof testing process as discussed herein. Additionally, ball bearing 534 is configured to rotate and/or move within probe 504. As discussed herein, ball bearing 534 ability to rotate within probe 504 allows probe 504, and specifically circular contact portion 530 formed on ball bearing 534, to both contact brittle component 502 to apply a force when proof testing brittle component 502 and also roll along brittle component 502 (e.g., not be lifted) when moving from the first location and the second location on brittle component 502. This allows probe 504 the ability to proof test the brittle component 502 at both the first and second location, as well as, the portions of brittle component 502 positioned between the first and second location that probe rolls over, as discussed herein.

Figure 6A:
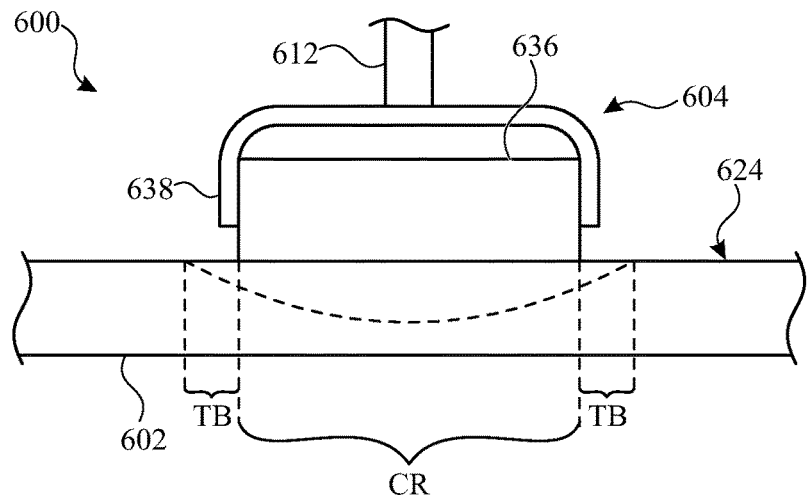
FIG. 6A shows a front view of a test probe of a testing system and a portion of a brittle component for an electronic device, according to another embodiment.
Figure 6B:
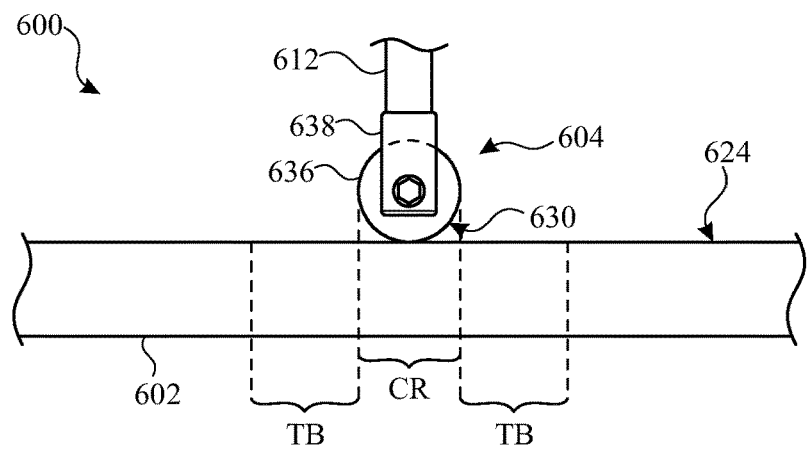
FIG. 6B shows a side view of the test probe of the testing system and a portion of the brittle component for an electronic device of FIG. 6A, according to another embodiment.
Figure 6C:
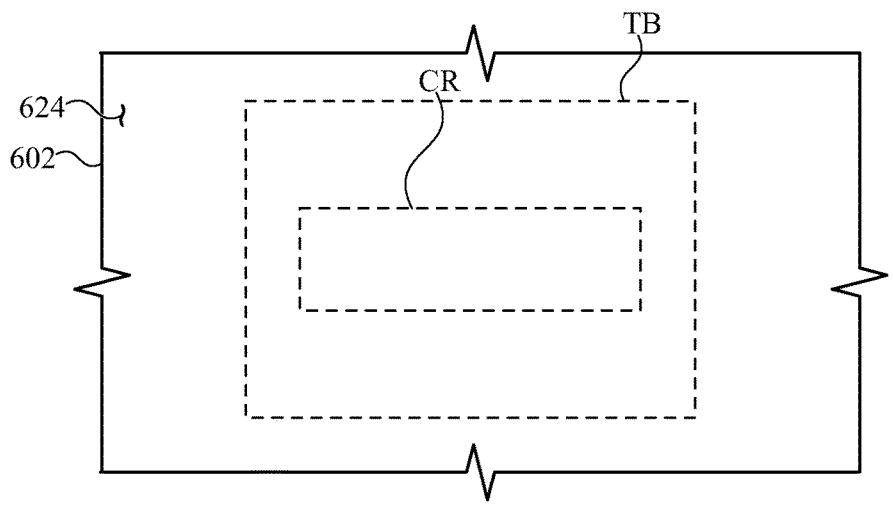
FIG. 6C shows a top view of a contact area formed on the brittle component by the test probe of FIG. 6A, according to embodiments.

FIGS. 6A-6C shows another non-limiting example of probe 604 of testing system 600, probe 604 contacting brittle component 602. Probe 604 is omitted from FIG. 6C for clarity. In the non-limiting example, probe 604 includes a rotatable cylinder 636 configured to form a substantially linear contact area on brittle component 602. As shown in FIGS. 6A and 6B, rotatable cylinder 636 is coupled to piston 612 via bracket 638. Rotatable cylinder 636 is coupled to bracket 638 using any conventional coupling components and/or techniques that allows rotatable cylinder 636 to rotate as probe 604 moves over brittle component 602, as discussed herein. As similarly discussed herein, piston 612, in combination with a gantry system (see, FIG. 1A), is configured to move rotatable cylinder 636 in a first direction ($D_1$), a second direction ($D_2$), and a third direction ($D_3$) (see, FIGS. 1A and 1B) to perform the proof testing process. Additionally in a non-limiting example, piston 612 is also configured to rotate rotatable cylinder 636.

As shown in FIG. 6B, rotatable cylinder 636 forming probe 604 includes substantially spherical or circular contact portion 630. Substantially spherical or circular contact portion 630 of rotatable cylinder 636 contacts contact surface 624 when probe 604 applies a force to brittle component 602 during the proof testing process discussed herein. Additionally, because of the elongated shape of rotatable cylinder 636, the contact area formed between rotatable cylinder 636 and brittle component 602 is also substantially elongated and linear.

As previously discussed herein with respect to FIGS. 2A and 2B, when probe 604 contacts brittle component 602 and applies a force during the proof testing process, portions of brittle component 602 formed below contact surface 624 and/or probe 604 are affected. In a non-limiting example shown in FIGS. 6A-6C, a compressed region (CR) is formed in a portion of brittle component 602 when probe 604 applies a force to brittle component 602. As shown in FIGS. 6A and 6B, the compressed region (CR) is formed below contact surface 624, and is substantially aligned with probe 604 contacting brittle component 602. Additionally, in the non-limiting example shown in FIGS. 6A and 6B, because rotatable cylinder 634 forming probe 604 has a greater length (see, FIG. 6A) than width (see, FIG. 6B), the compressed region (CR) also has a greater length than width.

In the non-limiting example shown in FIGS. 6A-6C, localized tensile band (TB) is also formed within a portion of brittle component 602 when probe 604 applies a force to brittle component 602. The tensile band (TB) is formed below contact surface 624, and is formed substantially adjacent probe 604 contacting brittle component 602. As shown in FIGS. 6A-6C, the tensile band (TB) is also positioned adjacent to and/or substantially surrounds compressed region (CR) formed in brittle component 602. The tensile band (TB) is formed in brittle component 602 as a result of forming compressed region (CR) in brittle component 602 when the force is applied by probe 604.

As shown in FIGS. 6A-6C, the tensile band (TB) formed in brittle component 602 is substantially larger than the compressed region (CR). Specifically, the portions of tensile band (TB) formed on opposite sides of the compressed region (CR), and adjacent substantially circular contact portion 630 are substantially larger than the compressed region (CR). Additionally, the portions of tensile band (TB) formed on opposite sides of the compressed region (CR), and adjacent substantially circular contact portion 630 are substantially larger than the remaining portions of the tensile band (TB) positioned adjacent bracket 638 and/or the ends of rotatable cylinder 636. The tensile band (TB) is smaller on the portions adjacent bracket 638 and/or the ends of rotatable cylinder 636 as a result of rotatable cylinder 636 having substantially flat or linear ends that are formed perpendicular to contact surface 624 of brittle component 602.

Additionally, as shown in FIGS. 6A and 6B, the depth or magnitude of the tensile band (TB) decreases as the distance from the compressed region (CR) increases. Specifically, at the transition line between the compressed region (CR) and the tensile band (TB), the depth or magnitude of each of the compressed region (CR) and tensile band (TB) is substantially equal. However, as the distance within the tensile band (TB) increases from the compressed region (CR), the depth or magnitude of the tensile band decreases. As discussed herein, the size, width, depth and/or magnitude of the compressed region (CR) and tensile band (TB) formed in brittle component 602 when probe 604 applies a force is dependent on, at least in part, the size of probe 604 and/or contact portion 630, the shape of contact portion 630 of probe 604, the material composition of brittle component 602, the magnitude of the force applied by probe 604 and so on.

Figure 7:
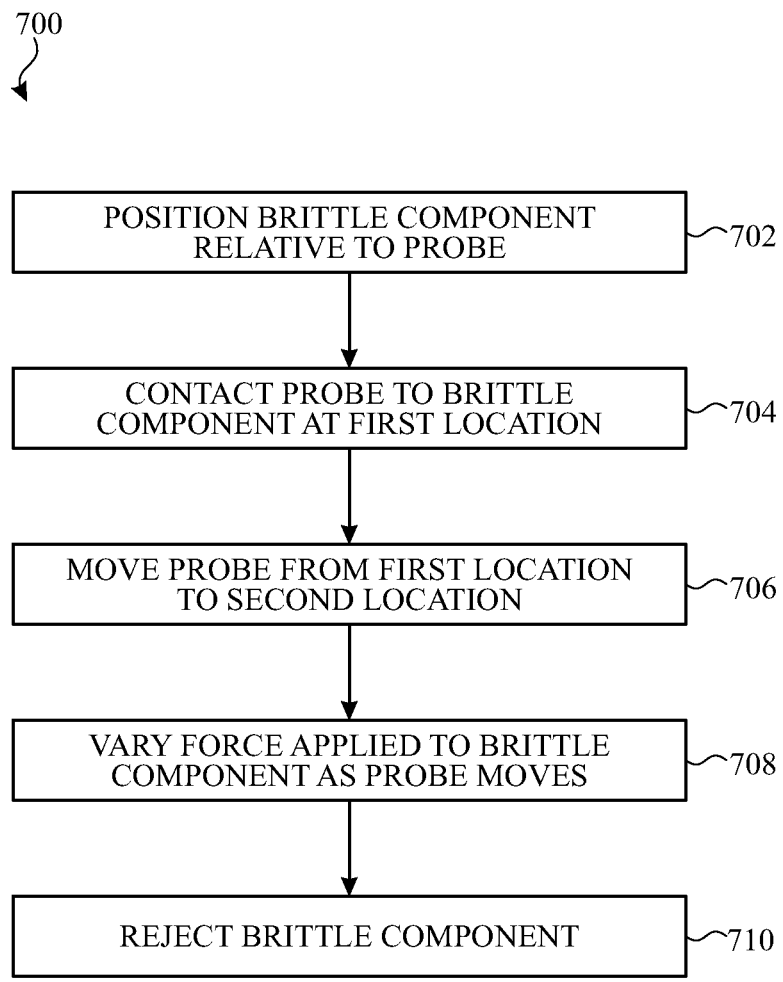
FIG. 7 shows a flow chart of an example process for proof testing brittle components for an electronic device, according to additional embodiments.

FIG. 7 depicts an example process for proof testing a component. Specifically, FIG. 7 is a flowchart depicting one example process 700 for proof testing a brittle component for an electronic device. In some cases, the brittle component is formed from a ceramic material, as discussed herein respect to FIGS. 1A and 1B and can be utilized within an electronic device discussed below with respect to FIG. 9.

In process 702, a brittle component utilized by an electronic device is positioned relative to a probe of a testing system. The brittle component can include surface defects (e.g., chips, cracks) that are undetected and/or invisible when performing a visual inspection of the brittle component. The surface defects are formed on a surface and/or partially through the brittle component. The brittle component can be formed from a brittle ceramic material including, but not limited to, alumina, sapphire or zirconia.

Positioning the brittle component relative to the probe can also include securing the brittle component to a rigid base support and/or preventing or restraining edges of the brittle component from bending when a force is applied to the brittle component by the probe, as similarly discussed herein with respect to process 302 of FIG. 3. Redundant explanation of these components and/or process(es) has been omitted for clarity.

In process 704, the probe of the testing system contacts the brittle component at a first location. Specifically, the probe is moved to contact a surface of the brittle component at a first location of the brittle component. The probe is moved to contact the brittle component at the first location by a gantry system. The first location of the brittle component which the probe contacts can be a random location on the brittle component or can be a predetermined location. Where the first location is predetermined, the first location can include a feature (e.g., aperture) formed in the brittle component, and/or can include a portion of the brittle component that is supported by internal components or portions of the electronic device. Additionally, the first location can also include a surface defect formed in the brittle component.

In process 706, the probe is moved from the first location on the surface of the brittle component to a second location on the brittle component, distinct from the first location. Specifically, the probe is moved from the first location to the second location, and remains in constant contact with the surface of the brittle component. The contact can be maintained as a result of the probe being formed from a substantially circular and rotatable cylinder or drum. The substantially circular and rotatable cylinder can roll along the surface of the brittle component from the first location to the second location. As discussed herein, the probe is moved using the gantry system.

In process 708, a force is applied to the brittle component as the probe moves over and maintains contact with the surface of the brittle component. Specifically, a varied force is applied to the brittle component as the probe moves from the first location to the second location. The first force is applied to the brittle component using the probe of the testing system. Applying the varied force to the brittle component also includes forming a compressed region and creating a localized tensile band in the brittle component. The compressed region is formed in the brittle component below and/or aligned with the probe contacting the surface of the brittle component. The tensile band is created below the surface of and/or partially within the brittle component. The tensile band is also positioned adjacent and/or substantially surrounds the compressed region created in the brittle component. Where the probe is configured as a substantially circular and rotatable cylinder, at least a portion of the localized tensile band is created and/or formed within the brittle component on opposite sides of the compressed region formed therein.

Applying the varied force in process 708 also includes applying a first force at the first location and applying a second force at the second location. The second force applied at the second location on the brittle component is either substantially similar or different than the first force applied to the first location. Varying the force applied to the brittle component can also include increasing or decreasing the force applied to the brittle component as the probe moves from the first location on the brittle component to the second component. Additionally, varying the force applied to the brittle component can include applying a greater force at the first location than a force applied at the second location. The magnitude of the varying force applied to the brittle component can be dependent upon the physical and/or material characteristics of the brittle component. Specifically, the physical and/or material characteristics of the brittle component in the first and second location determines whether or not the first location receives a greater force than the second location, and how the force varies as the probe is moved from the first location to the second location. The physical and/or material characteristics can include the thickness of the brittle component, features formed in the brittle component, which affect the strength of the brittle component, and/or the amount of support provided to the brittle component by internal components or portions of the electronic device. In a non-limiting example where the first location on the brittle component includes a stronger portion of the brittle component and/or is provided more support from other internal components of the electronic device, the force applied at the first location is greater than the force applied at the second location.

In process 710, the brittle component is rejected from use within an electronic device in response to a surface defect being propagated through at least a portion of the brittle component. Specifically, when the previously invisible or undetectable surface defect formed in the brittle component is propagated and/or becomes visible in response to applying the varied force and/or the first and second forces in process 708, the brittle component has failed the testing process. As such, the brittle component is discarded and/or not used within an electronic device because it does not meet the quality and/or strength standards for the electronic device, as discussed herein.

Figure 8A:
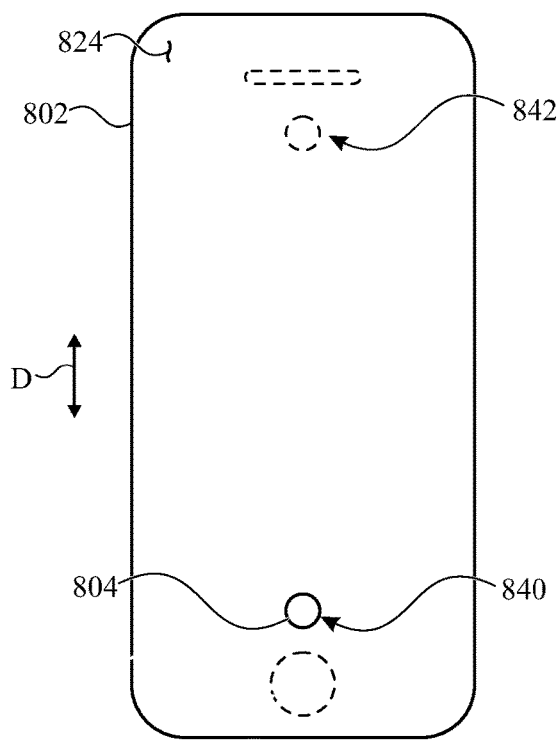
FIG. 8A shows a top view of a brittle component for an electronic device and a test probe contacting the brittle component, according to embodiments.
Figure 8B:
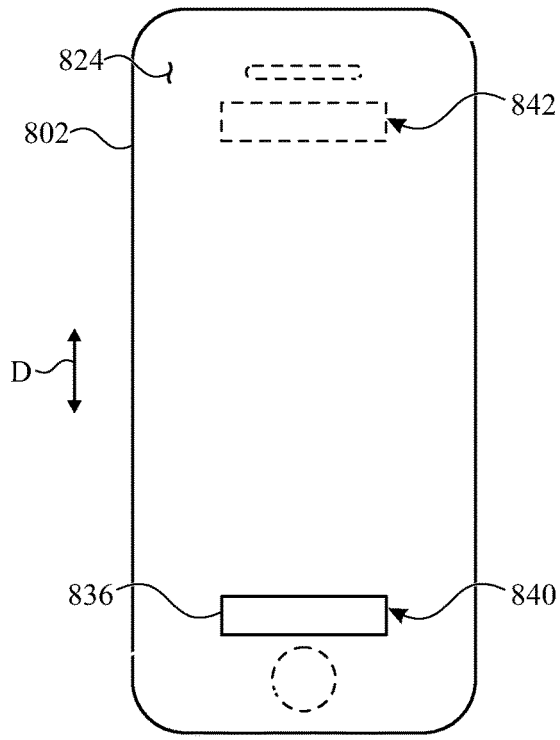
FIG. 8B shows a top view of a brittle component for an electronic device and a test probe contacting the brittle component, according to additional embodiments.

FIGS. 8A and 8B show top views of brittle component 802 and probe 804 or rotatable cylinder 836 performing a proof testing process 700 on brittle component 802 as similarly discussed herein with respect to FIG. 7. Probe 804 shown in FIG. 8A corresponds to probe 504 shown in FIG. 5 that includes ball bearing 534, and is configured to roll or move over contract surface 824 of brittle component 802 when performing the proof testing process 700. Additionally, FIG. 8B shows probe configured as rotatable cylinder 836, as similarly discussed herein with respect to FIGS. 6A-6C.

Brittle component 802 shown in FIGS. 8A and 8B include a first location 840 and a second location on brittle component 802. As similarly discussed above with respect to FIGS. 4A-4F, first location 840 and second location 842 include unique or distinct properties or characteristics which affect and/or influence the magnitude of the force applied to each location of brittle component 802. Continuing the example discussed above with respect to FIGS. 4A-4F, first location 840 can include a greater amount of support from additional components of the electronic device than second location 842 of brittle component 802, and first location 840 on the brittle component 802 can include a stronger portion of brittle component 802 than second location 842 of the brittle component 802. As such, the first force applied at first location 840 by probe 804/rotatable cylinder 836 is distinct (e.g., smaller, greater) than the second force applied at the second location 842 on brittle component 802.

Distinct from the example proof testing process 300 discussed above with respect to FIGS. 3-4F, probe 804 and rotatable cylinder 836 may not be lifted away from contact surface 824 when moving from first location 840 to second location 842. Specifically, probe 804 including a ball bearing (see, FIG. 5) and rotatable cylinder 836 (see, FIGS. 6A-6C) are configured to roll or move along contact surface 824. As a result, probe 804 and rotatable cylinder 836 maintain constant contact with contact surface 824 of brittle component 802 when moving or rolling from first location 840 to second location 842. In an example shown in FIGS. 8A and 8B, probe 804 and/or rotatable cylinder 836 can move from first location 840 to second location 842 in a direction (D). Although only a single direction (D) is shown in FIGS. 8A and 8B, it is understood that probe 804 and/or rotatable cylinder 836 can move in various directions when moving from first location 840 to second location 842 while maintaining contact with contact surface 824 (see, FIG. 1A). Allowing probe 804 and/or rotatable cylinder 836 to maintain contact with brittle component 802 as they move from first location 840 to second location 842 provides more areas and/or locations of brittle component 802 to be proof tested, which ultimately increases the accuracy and reliability of the proof test performed on brittle component 802.

While maintaining contact with contact surface 824 when moving from first location 840 to second location 842, probe 804/rotatable cylinder 836 can vary a force applied to brittle component 804 while probe 804/rotatable cylinder 836 are in motion. That is, probe 804/rotatable cylinder 836 can apply a varied force to the portions of brittle component 802 positioned between first location 840 and second location 842 as probe 804/rotatable cylinder 836 move from first location 840 to second location 842. The varied force applied to brittle component 802 can vary based on location or position of probe 804/rotatable cylinder 836 on brittle component 802 and/or the first force and second force applied to first location 840 and second location 842 respectively. In a non-limiting example where the first force applied to first location 840 is greater than the second force applied to the second location 842, probe 804/rotatable cylinder 836 can apply a decreasingly varied force as probe 804/rotatable cylinder 836 move from first location 840 to second location 842. In another non-limiting example where the first force applied to first location 840 is less than the second force applied to the second location 842, probe 804/rotatable cylinder 836 can apply an increasingly varied force as probe 804/rotatable cylinder 836 move from first location 840 to second location 842. In a further non-limiting example, the varied force can increase than decrease as probe 804/rotatable cylinder 836 move from first location 840 to second location 842.

As similarly discussed herein with respect to process 300 and FIGS. 4B-4F, moving probe 804/rotatable cylinder 836 over and maintaining contact with contact surface 824 while applying a varied force to brittle component 802 can result in the propagation of surface defects (e.g., crack, chips) formed in brittle component 802. Where the surface defects propagate and become visible and/or impact the physical properties or characteristics of brittle component 802, brittle component 802 can be rejected from implementation within an electronic device and is discarded.

The processes performed on brittle component 802 as shown and discussed herein with respect to FIGS. 8A and 8B, correspond to operations 702, 704, 706, 708 and 710 of the process 700 shown in FIG. 7.

Figure 9:
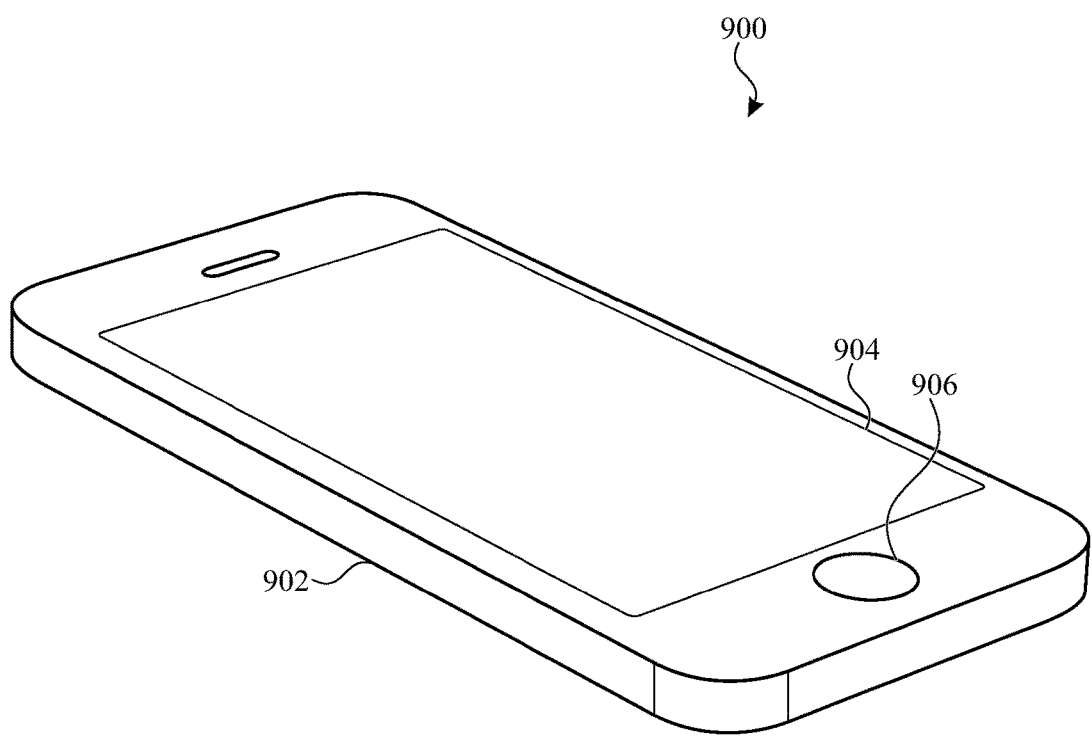
FIG. 9 shows an electronic device utilizing a brittle component, according to embodiments.

FIG. 9 shows an electronic device 900 that utilizes a brittle component discussed herein with respect to FIGS. 1A-8B. Specifically, electronic device 900 includes various brittle components that are formed from the ceramic materials that undergo the proof testing process using the testing system discussed herein to ensure each brittle component of electronic device 900 meets a quality and/or strength standard. By meeting the quality and/or strength standard for electronic device 900, the brittle component of electronic device 900 formed from the ceramic material includes desired functional, operational and/or physical characteristics and properties. As shown in FIG. 9, electronic device 900 is implemented as a mobile phone. Other embodiments can implement electronic device 900 differently, such as, for example, as a laptop or desktop computer, a tablet computing device, a gaming device, a display, a digital music player, a wearable computing device or display, a health monitoring device, and so on.

Electronic device 900 includes a housing 902 at least partially surrounding a display module, a cover 904 substantially covering the display module and one or more buttons or input devices 906. Housing 902 can form an outer surface or partial outer surface and protective case for the internal components of the electronic device 900 and at least partially surrounds the display module positioned within an internal cavity formed by housing 902. Housing 902 can be formed of one or more components operably connected together, such as a front piece and a back piece (not shown). Alternatively, housing 902 can be formed of a single piece operably connected to the display module. Housing 902 is formed from the ceramic material discussed herein, and as a result, undergoes the proof testing process using the testing system prior to being implemented in and/or forming a portion of electronic device 900.

The display module is substantially surrounded by housing 902 and/or is positioned within an internal cavity formed by housing 902, such that the display module is substantially protected on almost all sides by housing 902. Cover 904 also protects the display module of electronic device 900. Specifically, cover 904 is formed integral with and/or is coupled to housing 902 to substantially cover and protect the display module. Cover 904 covers at least a portion of the front surface of electronic device 900. When a user interacts with the display module of electronic device 900, the user touches or contacts cover 904. Similar to housing 902, cover 904 of electronic device 900 can be a brittle component and is therefore formed from the ceramic material discussed herein. The ceramic material forming cover 904 can undergo the proof testing process performed by the testing system discussed herein with respect to FIGS. 1A-8B. By performing the proof testing process on the ceramic material forming cover 904, it is ensured that the ceramic material forming cover 904 meets the quality and/or strength standard required for implementation within electronic device 900 and/or cover 904 and includes desired functional, operational and/or physical characteristics and properties.

Button 906 can take the form of a home button, which may be a mechanical button, a soft button (e.g., a button that does not physically move but still accepts inputs), an icon or image on a display, and so on. Further, in some embodiments, button 906 can be integrated as part of cover 904 of the electronic device 900. Button 906, like housing 902 and cover 904, is a brittle component of electronic device 900 and, as a result, is formed from the ceramic material that undergoes the proof testing process as discussed herein.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A method for proof testing a brittle component for an electronic device, comprising:
    positioning a probe of a testing system relative to the brittle component, the brittle component being supported by a base support;
    contacting the probe to a surface of the brittle component at a first location;
    applying a first compressive force at the first location using the probe to create a first localized tensile band below the surface of the brittle component;
    contacting the probe to the surface of the brittle component at a second location, distinct from the first location; and
    applying a second compressive force at the second location using the probe to create a second localized tensile band below the surface of the brittle component.

2. The method of claim 1, further comprising:
    moving the probe from the first location on the surface of the brittle component to the second location; and
    maintaining contact between the surface of the brittle component and the probe as the probe moves from the first location to the second location.

3. The method of claim 1, further comprising rejecting the brittle component in response to at least one of the first applied compressive force or the second applied compressive force propagating a surface defect through at least a portion of the brittle component.

4. The method of claim 1, wherein: applying the first compressive force at the first location comprises applying the first compressive force to the brittle component for a predetermined time; and
    the predetermined time is dependent upon at least one of:
        operational characteristics of the testing system; or
        material characteristics of the brittle component.

5. The method of claim 1, wherein applying the first compressive force at the first location comprises forming a first compressed region in the brittle component, the first compressed region aligned with the probe.

6. The method of claim 5, wherein applying the first compressive force at the first location further comprises forming tensile band substantially surrounding the compressed region.

7. The method of claim 1, wherein positioning the brittle component relative to the probe comprises securing the brittle component to a rigid base support.

8. The method of claim 1, wherein positioning the brittle component relative to the probe comprises preventing edges of the brittle component from bending when the first compressive force is applied and the second compressive force is applied.

9. A method for proof testing a brittle component for an electronic device, comprising:
    positioning the brittle component relative to a probe of a testing system, the probe including a rotatable contact portion configured to contact and roll over a surface of the brittle component and to apply a force to the brittle component while rolling;
    contacting a surface of the brittle component at a first location with the probe;
    moving the probe from the first location to a second location on the surface of the brittle component while maintaining contact between the rotatable contact portion of the probe and the surface; and
    varying a force applied to the brittle component as the probe moves from the first location to the second location to create a localized tensile band below the surface of the brittle component.

10. The method of claim 9, wherein varying the force applied to the brittle component comprises forming a compressed region in the brittle component, and aligned with the probe.

11. The method of claim 10, wherein varying the force applied to the brittle component to create the localized tensile band comprises one of:
    forming the localized tensile band around the compressed region formed in the brittle component; or
    forming the localized tensile band on opposite sides of the compressed region formed in the brittle component.

12. The method of claim 9, wherein varying the force applied to the brittle component comprises:
    applying a first force at the first location; and
    applying a second force at the second location, the second force distinct from the first force.

13. The method of claim 12, wherein varying the force applied to the brittle component comprises one of:
    increasing the force applied to the brittle component as the probe moves from the first location to the second location; or
    decreasing the force applied to the brittle component as the probe moves from the first location to the second location.

14. The method of claim 9, wherein varying the force applied to the brittle component comprises:

applying a greater force at the first location than a force applied at the second location; wherein the first location comprises a stronger portion of the brittle component than the second location.

15. A system for proof testing a brittle component, comprising:
   a rigid base support configured to receive the brittle component;
   perimeter supports substantially surrounding the brittle component, the perimeter supports configured to apply a clamping force on the brittle component toward the rigid base support;
   a probe positioned above the rigid base support, the probe including a rotatable contact portion configured to contact and roll over a surface of the brittle component and to apply a force to the brittle component while rolling; and
   a gantry system coupled to the probe and configured to move the probe above the rigid base support.

16. The system of claim 15, wherein the rotatable contact portion of the probe comprises a substantially spherical contact portion configured to form a substantially circular contact area on the brittle component.

17. The system of claim 16, wherein the substantially spherical contact portion of the probe comprises a ball bearing.

18. The system of claim 15, wherein the rigid base support is configured to move the brittle component below the probe.

19. The system of claim 15, wherein the probe is configured to:
   form a compressed region within the brittle component, the compressed region aligned with the probe contacting the brittle component; and
   form a localized tensile band within the brittle component, the localized tensile band positioned substantially adjacent the compressed region.

* * * * *